United States Patent
Verboom et al.

(10) Patent No.: US 8,277,788 B2
(45) Date of Patent: Oct. 2, 2012

(54) QUICK DISPERSING HAIR CONDITIONING COMPOSITION

(75) Inventors: Gilles Verboom, St. Charles, IL (US); Randy Schueller, Park Ridge, IL (US)

(73) Assignee: Conopco, Inc., Englewood Cliffs, NJ (US)

( * ) Notice: Subject to any disclaimer, the term of this patent is extended or adjusted under 35 U.S.C. 154(b) by 791 days.

(21) Appl. No.: 11/195,966

(22) Filed: Aug. 3, 2005

(65) Prior Publication Data

US 2007/0031369 A1    Feb. 8, 2007

(51) Int. Cl.
*A61Q 5/12* (2006.01)
*A61K 8/00* (2006.01)

(52) U.S. Cl. .................. 424/70.27; 424/70.19
(58) Field of Classification Search .................. None
See application file for complete search history.

(56) References Cited

U.S. PATENT DOCUMENTS

| | | |
|---|---|---|
| 3,766,267 A | 10/1973 | Zak et al. |
| 3,822,312 A | 7/1974 | Sato et al. |
| 4,096,243 A | 6/1978 | Feinland et al. |
| 4,119,399 A | 10/1978 | Feinland et al. |
| 4,126,586 A | 11/1978 | Curtis et al. |
| 4,152,272 A | 5/1979 | Young |
| 4,159,260 A | 6/1979 | Jones et al. |
| 4,160,823 A | 7/1979 | Watanabe et al. |
| 4,165,369 A | 8/1979 | Watanabe et al. |
| 4,203,852 A | 5/1980 | Johnson et al. |
| RE30,874 E | 3/1982 | Dasher et al. |
| 4,402,700 A | 9/1983 | Feinland et al. |
| 4,415,701 A | 11/1983 | Bauer |
| 4,436,722 A | 3/1984 | Matsunaga et al. |
| 4,452,732 A | 6/1984 | Bolich, Jr. |
| 4,493,824 A | 1/1985 | Abe |
| 4,529,586 A | 7/1985 | De Marco et al. |
| 4,532,127 A | 7/1985 | Feinland et al. |
| 4,534,877 A | 8/1985 | Russell et al. |
| 4,537,762 A | 8/1985 | Fogel et al. |
| 4,584,356 A | 4/1986 | Crivello |
| 4,610,874 A | 9/1986 | Matravers |
| 4,636,329 A | 1/1987 | Steuri |
| 4,659,777 A | 4/1987 | Riffle et al. |

(Continued)

FOREIGN PATENT DOCUMENTS

DE    199 62 874 A1    6/2001

(Continued)

OTHER PUBLICATIONS

"Poucher's Perfumes, Cosmetics, and Soaps" 10th Edition, (2000) Edited by Hilda Butler, Kluwer Academic Publishers, pp. 255-287.*

(Continued)

*Primary Examiner* — Brian Gulledge
(74) *Attorney, Agent, or Firm* — Ronald A. Koatz

(57) ABSTRACT

Disclosed is a quick dispersing hair conditioning composition comprising (a) an isostearamidopropyl ethyldimethylammonium salt or a dicocodimethylammonium salt; (b) one or more fatty alcohols; (c) dimethicone; and (d) water. The hair conditioning composition of the invention has one or more advantageous properties. For example, an embodiment of the invention has a dispersion rate such that when 1.5 mL of the composition is dispersed into 400 mL of water at about 35° C. to about 40° C., the dispersion has a transmittance at 420 nm that is less than about 70% of the water at the same temperature in less than about 120 seconds.

12 Claims, 1 Drawing Sheet

Dispersion Profiles

U.S. PATENT DOCUMENTS

| | | | |
|---|---|---|---|
| 4,689,289 A | 8/1987 | Crivello |  |
| 4,693,935 A | 9/1987 | Mazurek |  |
| 4,719,104 A | 1/1988 | Patel |  |
| 4,726,945 A | 2/1988 | Patel et al. |  |
| 4,728,571 A | 3/1988 | Clemens et al. |  |
| 4,733,677 A | 3/1988 | Gee et al. |  |
| 4,751,074 A | 6/1988 | Matsunaga et al. |  |
| 4,753,793 A | 6/1988 | Walton |  |
| 4,765,975 A | 8/1988 | Iovanni et al. |  |
| 4,777,037 A | 10/1988 | Wagman et al. |  |
| 4,824,602 A | 4/1989 | Juneja |  |
| 4,859,457 A | 8/1989 | Suzuki et al. |  |
| 4,871,529 A | 10/1989 | Sramek |  |
| 4,891,214 A | 1/1990 | Stevens et al. |  |
| 4,892,728 A | 1/1990 | Kawa et al. |  |
| 4,892,729 A | 1/1990 | Cavazza |  |
| 4,906,459 A | 3/1990 | Cobb et al. |  |
| 4,910,013 A | 3/1990 | Kanamaru et al. |  |
| 4,911,919 A | 3/1990 | Patel et al. |  |
| 4,919,923 A | 4/1990 | Hoeffkes et al. |  |
| 4,954,335 A | 9/1990 | Janchipraponvej |  |
| 4,975,274 A | 12/1990 | Iannucci et al. |  |
| 4,976,956 A | 12/1990 | Noe |  |
| 5,017,221 A | 5/1991 | Legrow et al. |  |
| 5,032,460 A | 7/1991 | Kantner et al. |  |
| 5,034,218 A * | 7/1991 | Duvel | 424/70.12 |
| 5,089,252 A | 2/1992 | Grollier et al. |  |
| 5,114,706 A | 5/1992 | Duvel |  |
| 5,213,793 A | 5/1993 | Moses et al. |  |
| 5,240,698 A | 8/1993 | Traver et al. |  |
| 5,244,598 A | 9/1993 | Merrifield et al. |  |
| 5,277,899 A | 1/1994 | McCall |  |
| 5,288,484 A | 2/1994 | Tashjian |  |
| 5,298,240 A | 3/1994 | Schröder et al. |  |
| 5,306,434 A | 4/1994 | Schueller et al. |  |
| 5,306,489 A | 4/1994 | Goldberg et al. |  |
| 5,330,758 A | 7/1994 | Hansenne-Richoux et al. |  |
| 5,332,569 A | 7/1994 | Wood et al. |  |
| 5,358,667 A | 10/1994 | Bergmann |  |
| 5,362,485 A | 11/1994 | Hayama et al. |  |
| 5,380,528 A | 1/1995 | Alban et al. |  |
| 5,393,452 A | 2/1995 | Raleigh et al. |  |
| 5,403,517 A | 4/1995 | Horinishi et al. |  |
| 5,415,857 A | 5/1995 | Robbins et al. |  |
| 5,454,841 A | 10/1995 | Wolfram et al. |  |
| 5,456,863 A * | 10/1995 | Bergmann | 510/122 |
| 5,468,477 A | 11/1995 | Kumar et al. |  |
| 5,494,533 A | 2/1996 | Woodin, Jr. et al. |  |
| 5,523,365 A | 6/1996 | Geck et al. |  |
| 5,547,990 A | 8/1996 | Hall et al. |  |
| 5,562,898 A * | 10/1996 | Dowell et al. | 424/70.1 |
| 5,578,298 A | 11/1996 | Berthiaume et al. |  |
| 5,589,177 A | 12/1996 | Herb et al. |  |
| 5,610,201 A | 3/1997 | Grollier et al. |  |
| 5,618,524 A | 4/1997 | Bolich, Jr. et al. |  |
| 5,656,280 A | 8/1997 | Herb et al. |  |
| 5,658,557 A | 8/1997 | Bolich, Jr. et al. |  |
| 5,658,577 A | 8/1997 | Fowler et al. |  |
| 5,683,683 A | 11/1997 | Scafidi |  |
| 5,707,612 A | 1/1998 | Zofchak et al. |  |
| 5,714,136 A | 2/1998 | Yahagi et al. |  |
| 5,756,076 A | 5/1998 | Cervantes et al. |  |
| 5,756,108 A | 5/1998 | Ribier et al. |  |
| 5,759,557 A | 6/1998 | Epstein et al. |  |
| 5,807,545 A | 9/1998 | Coffindaffer et al. |  |
| 5,830,483 A | 11/1998 | Seidel et al. |  |
| 5,843,418 A | 12/1998 | Coffindaffer et al. |  |
| 5,849,280 A | 12/1998 | Rechelbacher et al. |  |
| 5,849,281 A | 12/1998 | Babinski et al. |  |
| 5,855,878 A | 1/1999 | Coffindaffer et al. |  |
| 5,891,954 A | 4/1999 | Gee et al. |  |
| 5,925,341 A | 7/1999 | Cervantes et al. |  |
| 5,942,216 A | 8/1999 | Herb et al. |  |
| 5,955,066 A | 9/1999 | Sako et al. |  |
| 5,961,990 A | 10/1999 | Delrieu et al. |  |
| 5,961,991 A | 10/1999 | Wenke et al. |  |
| 5,965,115 A | 10/1999 | Bolich, Jr. et al. |  |
| 5,968,495 A | 10/1999 | Bolich, Jr. et al. |  |
| 5,972,356 A | 10/1999 | Peffly |  |
| 5,985,255 A | 11/1999 | Vanlerberghe et al. |  |
| 5,985,294 A | 11/1999 | Peffly |  |
| 5,989,533 A | 11/1999 | Deegan et al. |  |
| 5,997,851 A | 12/1999 | Cox et al. |  |
| 5,997,854 A | 12/1999 | Von Mallek |  |
| 5,997,886 A | 12/1999 | Peffly et al. |  |
| 6,022,547 A | 2/2000 | Herb et al. |  |
| 6,071,524 A | 6/2000 | Ribier et al. |  |
| 6,071,975 A | 6/2000 | Halloran |  |
| 6,106,814 A * | 8/2000 | Raney et al. | 424/70.1 |
| 6,110,450 A | 8/2000 | Bergmann |  |
| 6,147,038 A | 11/2000 | Halloran |  |
| 6,149,898 A | 11/2000 | Peffly et al. |  |
| 6,149,899 A | 11/2000 | Pyles |  |
| 6,156,076 A | 12/2000 | Casperson et al. |  |
| 6,156,297 A | 12/2000 | Maurin et al. |  |
| 6,235,275 B1 | 5/2001 | Chen et al. |  |
| 6,274,126 B1 | 8/2001 | Newell et al. |  |
| 6,274,128 B1 | 8/2001 | Bergmann et al. |  |
| 6,287,545 B1 | 9/2001 | Su |  |
| 6,287,547 B1 | 9/2001 | Oota et al. |  |
| 6,288,137 B1 | 9/2001 | Iliopoulos et al. |  |
| 6,294,159 B1 * | 9/2001 | Reich et al. | 424/70.12 |
| 6,319,507 B1 | 11/2001 | Delrieu et al. |  |
| 6,322,778 B1 | 11/2001 | Parr et al. |  |
| 6,383,477 B1 | 5/2002 | Lede et al. |  |
| 6,437,008 B1 | 8/2002 | Ikeda et al. |  |
| 6,458,343 B1 | 10/2002 | Zeman et al. |  |
| 6,462,009 B1 | 10/2002 | Nagy et al. |  |
| 6,468,515 B1 | 10/2002 | Uchiyama et al. |  |
| 6,475,974 B1 | 11/2002 | Leboucher et al. |  |
| 6,482,399 B2 | 11/2002 | Pyles |  |
| 6,488,780 B2 | 12/2002 | Cauwet-Martin |  |
| 6,491,902 B2 | 12/2002 | Shefer et al. |  |
| 6,495,498 B2 | 12/2002 | Niemiec et al. |  |
| 6,537,533 B2 | 3/2003 | Alvarado |  |
| 6,540,989 B2 | 4/2003 | Janchitraponvej |  |
| 6,552,171 B2 * | 4/2003 | Howard et al. | 530/377 |
| 6,559,189 B2 | 5/2003 | Baker, Jr. et al. |  |
| 6,562,328 B2 | 5/2003 | Pereira et al. |  |
| 6,572,846 B2 | 6/2003 | Klein |  |
| 6,582,710 B2 | 6/2003 | Deckers et al. |  |
| 6,586,378 B2 | 7/2003 | Chandra |  |
| 6,589,509 B2 | 7/2003 | Keller et al. |  |
| 6,589,517 B1 | 7/2003 | McKelvey et al. |  |
| 6,602,494 B1 | 8/2003 | Jahedshoar et al. |  |
| 6,607,717 B1 | 8/2003 | Johnson et al. |  |
| 6,607,718 B1 | 8/2003 | Okuno et al. |  |
| 6,610,280 B2 | 8/2003 | Ainger et al. |  |
| 6,613,316 B2 | 9/2003 | Sun et al. |  |
| 6,616,922 B2 | 9/2003 | Taylor et al. |  |
| 6,619,295 B1 | 9/2003 | Okabe et al. |  |
| 6,635,262 B2 | 10/2003 | Jourdan et al. |  |
| 6,638,497 B2 | 10/2003 | Barinova et al. |  |
| 6,645,480 B2 | 11/2003 | Giles |  |
| 6,645,507 B2 | 11/2003 | Bettle et al. |  |
| 6,685,926 B2 | 2/2004 | Hehner et al. |  |
| 6,685,952 B1 | 2/2004 | Ma et al. |  |
| 6,696,051 B2 | 2/2004 | Barbuzzi et al. |  |
| 6,696,052 B2 | 2/2004 | Aeby et al. |  |
| 6,696,053 B1 | 2/2004 | Ma et al. |  |
| 6,709,663 B2 | 3/2004 | Espinoza |  |
| 6,726,903 B2 | 4/2004 | Rutherford et al. |  |
| 6,730,292 B1 | 5/2004 | Yang et al. |  |
| 6,730,641 B2 | 5/2004 | Verboom et al. |  |
| 6,737,046 B2 | 5/2004 | Schmenger et al. |  |
| 6,800,293 B1 | 10/2004 | Farby et al. |  |
| 6,824,764 B2 | 11/2004 | Devin-Baudoin et al. |  |
| 6,824,765 B2 | 11/2004 | Gawtrey et al. |  |
| 6,858,202 B2 | 2/2005 | Niemiec et al. |  |
| 6,881,399 B2 | 4/2005 | Milbradt et al. |  |
| 2001/0004632 A1 | 6/2001 | Giles |  |
| 2001/0014317 A1 | 8/2001 | Pyles |  |
| 2001/0022967 A1 | 9/2001 | Brandt et al. |  |
| 2001/0028887 A1 | 10/2001 | Douin et al. |  |
| 2001/0031270 A1 | 10/2001 | Douin et al. |  |
| 2001/0036448 A1 | 11/2001 | Pereira et al. |  |
| 2001/0053374 A1 | 12/2001 | Dalrymple et al. |  |

| | | |
|---|---|---|
| 2002/0001605 A1 | 1/2002 | Carew et al. |
| 2002/0006389 A1 | 1/2002 | Restle et al. |
| 2002/0012650 A1 | 1/2002 | Klein |
| 2002/0015685 A1 | 2/2002 | Pascual et al. |
| 2002/0015686 A1 | 2/2002 | Pyles |
| 2002/0031478 A1 | 3/2002 | Keller et al. |
| 2002/0031487 A1 | 3/2002 | Klein |
| 2002/0034487 A1 | 3/2002 | Maubru et al. |
| 2002/0045667 A1 | 4/2002 | Baker, Jr. et al. |
| 2002/0076388 A1 | 6/2002 | Newell et al. |
| 2002/0106343 A1 | 8/2002 | Sun et al. |
| 2002/0143063 A1 | 10/2002 | Alvarado |
| 2002/0146379 A1 | 10/2002 | Shefer et al. |
| 2002/0146381 A1 | 10/2002 | Aeby et al. |
| 2002/0151446 A1 | 10/2002 | Piterski et al. |
| 2003/0012763 A1 | 1/2003 | Barinova et al. |
| 2003/0021759 A1 | 1/2003 | Milbradt et al. |
| 2003/0022941 A1 | 1/2003 | Taylor et al. |
| 2003/0026774 A1 | 2/2003 | Milbradt et al. |
| 2003/0039623 A1 | 2/2003 | Pyles |
| 2003/0053961 A1 | 3/2003 | Eccard |
| 2003/0053974 A1 | 3/2003 | Shefer et al. |
| 2003/0059382 A1 | 3/2003 | Brandt et al. |
| 2003/0068291 A1 | 4/2003 | Decoster et al. |
| 2003/0068292 A1 | 4/2003 | Pfaffernoschke et al. |
| 2003/0091523 A1 | 5/2003 | Dhamdhere et al. |
| 2003/0095943 A1 | 5/2003 | Barbuzzi et al. |
| 2003/0103927 A1 | 6/2003 | Maubru |
| 2003/0118543 A1 | 6/2003 | Pyles |
| 2003/0130162 A1 | 7/2003 | Llosas et al. |
| 2003/0140430 A1 | 7/2003 | Casperson et al. |
| 2003/0143181 A1 | 7/2003 | Hensen et al. |
| 2003/0147827 A1 | 8/2003 | Decoster et al. |
| 2003/0147842 A1 | 8/2003 | Restle et al. |
| 2003/0157049 A1 | 8/2003 | Gawtrey et al. |
| 2003/0161804 A1 | 8/2003 | Perron et al. |
| 2003/0162683 A1 | 8/2003 | Nagy et al. |
| 2003/0185869 A1 | 10/2003 | Wertz et al. |
| 2003/0190302 A1 | 10/2003 | Frantz et al. |
| 2003/0191035 A1* | 10/2003 | Verboom et al. ............... 510/119 |
| 2003/0198653 A1 | 10/2003 | Walele et al. |
| 2003/0215415 A1 | 11/2003 | Mitsumatsu et al. |
| 2003/0223952 A1 | 12/2003 | Wells et al. |
| 2004/0005287 A1 | 1/2004 | Rutherford et al. |
| 2004/0009141 A1 | 1/2004 | Koenig et al. |
| 2004/0052834 A1 | 3/2004 | West et al. |
| 2004/0062740 A1 | 4/2004 | Fan et al. |
| 2004/0071653 A1 | 4/2004 | Bratescu et al. |
| 2004/0076595 A1 | 4/2004 | Khan |
| 2004/0096416 A1 | 5/2004 | Fack et al. |
| 2004/0109840 A1 | 6/2004 | De Azevedo et al. |
| 2004/0131576 A1 | 7/2004 | Decoster et al. |
| 2004/0131577 A1 | 7/2004 | Davies et al. |
| 2004/0146480 A1 | 7/2004 | Prat Queralt et al. |
| 2004/0158939 A1 | 8/2004 | Wells et al. |
| 2004/0166084 A1 | 8/2004 | Sakai et al. |
| 2004/0223938 A1 | 11/2004 | Li et al. |
| 2005/0053570 A1 | 3/2005 | Hirai et al. |
| 2005/0063934 A1 | 3/2005 | Baker et al. |

FOREIGN PATENT DOCUMENTS

| | | | |
|---|---|---|---|
| EP | 0075475 A2 | | 3/1983 |
| EP | A2 0075475 | * | 3/1983 |
| EP | 0 268 982 A2 | | 6/1988 |
| EP | 0285574 A2 | | 10/1988 |
| EP | 0 418 986 A2 | | 3/1991 |
| EP | 0 459 500 B1 | | 12/1991 |
| EP | 0 463 431 A2 | | 1/1992 |
| EP | 0 560 516 A1 | | 9/1993 |
| EP | 0 875 500 A2 | | 11/1998 |
| JP | 57046910 | | 3/1982 |
| JP | 57126409 | | 8/1982 |
| JP | 57206605 | | 12/1982 |
| JP | 58032814 | | 2/1983 |
| JP | 59106412 | | 6/1984 |
| JP | 59181206 | | 10/1984 |
| JP | 61130208 | | 6/1986 |
| JP | 61152617 | | 7/1986 |
| JP | 61267505 | | 11/1986 |
| WO | WO 95/23581 A2 | | 9/1995 |
| WO | WO 97/14395 A1 | | 4/1997 |
| WO | WO 99/66888 A1 | | 12/1999 |
| WO | WO 01/91707 A1 | | 12/2001 |
| WO | WO 2004/000250 | * | 12/2003 |
| WO | WO 2004/000250 A1 | | 12/2003 |
| WO | WO 2004/105723 | * | 12/2004 |
| WO | WO 2004/105723 A1 | | 12/2004 |

OTHER PUBLICATIONS

TRESemme Conditioner Revitalizing, *Familymeds*, downloaded Apr. 7, 2005.
Beers et al., *Polymer Preprints*, 37 (1), 571-572 (1996).
Brandrup et al., *Polymer Handbook*, 2, 337-348 (1975).
Dahms et al., *Cosmetics & Toiletries*, 110, 91-100 (1995).
Nakagawa et al., *Polymer Preprints*, 37(2), 270-271 (1996).
Noll, *Chemistry and Technology of Silicones*, 373-376 (1968).
Nuyken et al., *Macromolecular Design: Concept and Practice*, 8, 313-358 (1994).
Pantene Pro-v, *Walgreens.com*, downloaded Apr. 7, 2005.
VO5 Conditioner Balsam & Protein, *Familymeds.com*, downloaded Apr. 7, 2005.

* cited by examiner

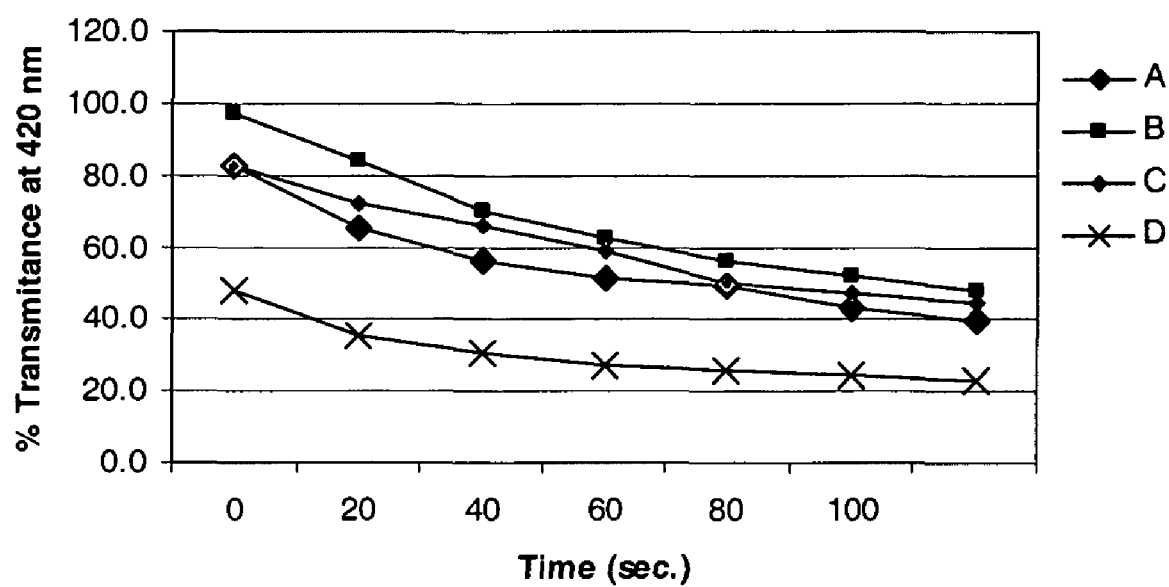

QUICK DISPERSING HAIR CONDITIONING COMPOSITION

BACKGROUND OF THE INVENTION

This invention relates to a hair conditioning composition, particularly one that is applied after shampooing.

Hair conditioning compositions are known. Hair conditioning compositions provide one or more of the following advantages: reduced static charge in the hair, reduced tangling of the hair, smoothness, softness, and silkiness of the hair, shine and sleekness of the hair, or manageability of the hair. The hair conditioning composition also should meet certain performance criteria such as rapid dispersion and distribution of the product upon the application of the composition on the hair. While one or more commercial hair conditioning compositions have acceptable application characteristics, there exists a need and desire to improve upon it further.

The present invention provides such a composition. This and other advantages of the invention as well as additional inventive features are set forth below.

BRIEF SUMMARY OF THE INVENTION

The foregoing need has been fulfilled to a great extent by the present invention which provides a quick dispersing hair conditioning composition. Accordingly, the present invention provides a hair conditioning composition comprising (a) an isostearamidopropyl ethyldimethylammonium salt or a dicocodimethylammonium salt; (b) one or more fatty alcohols; (c) dimethicone; and (d) water. The hair conditioning composition has one or more advantages, for example, quick dispersion in water and distribution onto the hair and good conditioning attributes. For example, the hair conditioning composition has a dispersion rate such that when 1.5 mL of the composition is dispersed into 400 mL of water at about 35° C. to about 45° C., the dispersion has a transmittance at 420 nm that is less than about 70% of the water at the same temperature in less than about 120 seconds.

BRIEF DESCRIPTION OF THE DRAWING

The FIGURE illustrates dispersion profiles of hair conditioning compositions of the invention. The x-axis represents time in seconds having a wavelength of 420 nm, and the y-axis represents percent transmittance of light.

DETAILED DESCRIPTION OF THE INVENTION

The present invention is predicated on the discovery that the presence of certain cationic surfactants, particularly an isostearamidopropyl ethyldimethylammonium salt or a dicocodimethylammonium salt, in the hair conditioning composition provides advantageous properties to the hair conditioning composition, for example, quick dispersion in water. Accordingly, the present invention provides, in an embodiment, a quick dispersing hair conditioning composition comprising (a) an isostearamidopropyl ethyldimethylammonium salt or a dicocodimethylammonium salt; (b) one or more fatty alcohols; (c) dimethicone; and (d) water.

The hair conditioning composition of the invention has a high dispersion rate. The dispersion rate in water can be expressed in any suitable manner, for example, by a property of the water when the composition is dispersed therein. Any suitable property can be used, for example, transmittance of light. Under this criterion, a quick dispersing composition will produce a dispersion that has less transmittance of light than a slow dispersing composition. The hair conditioning composition of the invention will cause the dispersion to increase in opacity in a shorter period of time than a slow dispersing hair conditioning composition. Thus, for example, a composition in accordance with an embodiment has a dispersion rate such that when 1.5 mL of the composition is dispersed into 400 mL of water at about 35° C. to about 40° C., the dispersion has a transmittance at 420 nm that is less than about 70% (e.g., less than about 65%, less than about 60%, less than about 55%, or less than about 50%) of the water at the same temperature in less than about 120 seconds (e.g., less than about 110 seconds, less than about 100 seconds, less than about 90 seconds, less than about 80 seconds, less than about 70 seconds, or less than about 60 seconds). In embodiments of the invention, the hair conditioning composition is non-transparent, e.g., opaque. Embodiments of the hair conditioning composition are applied after shampooing. Embodiments of the hair conditioning composition are free or substantially free of homopolymers of ethylene oxide or propylene oxide or copolymers of ethylene oxide and propylene oxide as well as of hydrolyzed protein, hydroxyethylcellulose, or polyvinylpyrrolidinone.

The isostearamidopropyl ethyldimethylammonium salt used in the composition of the invention can be any suitable salt. For example, the anion of the salt can be a halide, e.g., a bromide or chloride, a sulfate, for example, an alkylsulfate (e.g., ethosulfate), nitrate, or the like. Preferably, the salt used in the composition of the invention is the ethosulfate (i.e., isostearamidopropyl ethyldimethylammonium ethosulfate). The isostearamidopropyl ethyldimethylammonium salt can be present in any suitable amount. Preferably, the isostearamidopropyl ethyldimethylammonium salt is present in an amount of from about 0.1 wt. % to about 5 wt. % (e.g., from about 0.5 wt. % to about 4 wt. %, from about 1 wt. % to about 3 wt. %, or from about 1 wt. % to about 2 wt. %) of the hair conditioning composition. In a preferred embodiment, isostearamidopropyl ethyldimethylammonium ethosulfate is present in an amount of from about 0.1 wt. % to about 5 wt. % (e.g., from about 0.5 wt. % to about 4 wt. %, from about 1 wt. % to about 3 wt. %, or from about 1 wt. % to about 2 wt. %). An example of isostearamidopropyl ethyldimethylammonium ethosulfate is Mackernium CC-112P9 available from McIntyre Group Ltd.

The dicocodimethylammonium salt used in the composition of the invention can be any suitable salt. For example, the anion of the salt can be a halide, e.g., bromide or chloride, a sulfate, for example, an alkylsulfate (e.g., ethosulfate), nitrate, or the like. Preferably, the salt used in the composition of the invention is the chloride (i.e., dicocodimethylammonium chloride). Preferably, the dicocodimethylammonium salt is present in an amount of from about 0.1 wt. % to about 5 wt. % (e.g., from about 0.5 wt. % to about 4 wt. %, from about 1 wt. % to about 3 wt. %, or from about 1 wt. % to about 2 wt. %) of the hair conditioning composition. In a preferred embodiment, dicocodimethylammonium chloride is present in an amount of 0.1 wt. % to about 5 wt. % (e.g., from about 0.5 wt. % to about 4 wt. %, from about 1 wt. % to about 3 wt. %, or from about 1 wt. % to about 2 wt. %). A combination of the isostearamidopropyl ethyldimethylammonium salt and the dicocodimethylammonium salt can also be used in accordance with an embodiment of the invention. An example of dicocodimethylammonium chloride is Arquad 2C-70 available from Akzo-Nobel.

The one or more fatty alcohols used in the composition of the invention can be any suitable fatty alcohols. Preferably, the one or more fatty alcohols is a linear or branched, saturated or unsaturated $C_8$-$C_{24}$ fatty alcohol. For example, the one or more fatty alcohols can be selected from the group consisting of myristyl alcohol, cetyl alcohol, stearyl alcohol, oleyl alcohol, behenyl alcohol, or the like, and mixtures thereof. The one or more fatty alcohols can be present in any suitable amount. Preferably, at least one fatty alcohol is present in an amount of from about 0.1 wt. % to about 8 wt. % (e.g., from about 0.5 wt. % to about 6 wt. %, from about 0.5 wt. % to about 5 wt. %, from about 0.5 wt. % to about 4 wt. %, from about 1 wt. % to about 6 wt. %, from about 1 wt. % to about 5 wt. %, or from about 1 wt. % to about 4 wt. %). The composition contains a fatty alcohol selected from the group consisting of cetyl alcohol, for example, in an amount of from about 0.5 wt. % to about 4 wt. % (e.g., from about 1 wt. % to about 4 wt. %, from about 1 wt. % to about 3 wt. %, from about 1 wt. % to about 2 wt. %, or from about 2 wt. % to about 3 wt. %) and stearyl alcohol (particularly stearyl alcohol NF), for example, in an amount of from about 0.5 wt. % to about 4 wt. % (e.g., from about 1 wt. % to about 4 wt. %, from about 1 wt. % to about 3 wt. %, from about 1 wt. % to about 2 wt. %, or from about 2 wt. % to about 3 wt. %), or mixtures thereof. In a specific embodiment, the composition comprises about 2 wt. % cetyl alcohol and about 2 wt. % stearyl alcohol. In another embodiment, the composition comprises about 3 wt. % cetyl alcohol and about 1 wt. % stearyl alcohol.

The dimethicone, which is polydimethylsiloxane, can be present in any suitable amount. For example, the dimethicone can be present in an amount of from about 0.1 wt. % to about 3 wt. % (e.g., from about 0.1 wt. % to about 2 wt. %, from about 0.1 wt. % to about 1 wt. %, from about 0.5 wt. % to about 3 wt. %, from about 0.5 wt. % to about 2 wt. %, from about 0.5 wt. % to about 1 wt. %, from about 1 wt. % to about 3 wt. %, or from about 1 wt. % to about 2 wt. %) of the hair conditioning composition.

The water can be present in the composition of the invention in any suitable amount. For example, the water can be present in an amount greater than about 50% by wt/%, e.g., from about 50 wt. % to about 95 wt. % (e.g., from about 60 wt. % to about 95 wt. %, from about 70 wt. % to about 95 wt. %, from about 80 wt. % to about 95 wt. %, from about 70 wt. % to about 90 wt. %, from about 80 wt. % to about 90 wt. %, or from about 85 wt. % to about 90 wt. %) of the hair conditioning composition. Preferably, the composition of the invention comprises deionized water.

The quick dispersing hair conditioning composition of the invention can further include other ingredients suitable for hair conditioning compositions. The hair conditioning composition can include, but is not limited to, one or more ingredients selected from the group consisting of additional cationic surfactants, nonionic surfactants, thickeners, gelling agents, diluents (e.g., alcohols, glycols, and the like), vitamins (e.g., vitamin E), aloe, preservatives, emulsifiers, fragrances, and mixtures thereof.

Examples of suitable additional cationic surfactants can be monomeric, dimeric, trimeric, or polymeric and include, but are not limited to, quaternium-80 (sold as Abil-Quat 3272 by Degussa), cocotrimethylammonium chloride, cetyltrimethylammonium chloride, stearalkonium chloride, behenyl trimethylammonium chloride, dicetyl dimethylammonium chloride, tricetyl methylammonium chloride, dehydrogenated tallow dimethylammonium chloride (e.g., quaternium-18 which is sold as Varisoft 442-100P by Degussa), cocotrimethylammonium bromide, cetyltrimethylammonium bromide, stearalkonium bromide, behenyl trimethylammonium bromide, dicetyl dimethylammonium bromide, tricetyl methylammonium bromide, dehydrogenated tallow dimethylammonium bromide, cocotrimethylammonium methoxysulfate, cetyltrimethylammonium methoxysulfate, stearalkonium methoxysulfate, behenyl trimethylammonium methoxysulfate, dicetyl dimethylammonium methoxysulfate, tricetyl methylammonium methoxysulfate, dehydrogenated tallow dimethylammonium methoxysulfate, or the like, and mixtures thereof.

The additional cationic surfactant(s) can be present in any suitable amount. For example, the additional cationic surfactant(s) can be present in an amount of from about 0.01 wt. % to about 5 wt. % (e.g., from about 0.1 wt. % to about 4 wt. %, from about 0.1 wt. % to about 3 wt. %, from about 0.1 wt. % to about 2 wt. %, from about 0.1 wt. % to about 1 wt. %, from about 0.5 wt. % to about 3 wt. %, from about 0.5 wt. % to about 2 wt. %, or from about 1 wt. % to about 2 wt. %). In an embodiment, quaternium-18 is present in an amount of from about 1 wt. % to about 2 wt. %. In another embodiment, quaternium-80 is present in an amount of from 0.1 wt. % to about 0.5 wt. %.

Examples of suitable nonionic surfactants include, but are not limited to, the group consisting of fatty alcohol ethoxylates with an alkyl chain of $C_{14}$-$C_{18}$ and an ethoxylation degree that provides an HLB value of about 14 or higher, such as oleth-20, steareth-21, or the like, and mixtures thereof. The nonionic surfactant can be present in any suitable amount. For example, the nonionic surfactant can be present in an amount of from about 0.1 wt. % to about 3 wt. % (e.g., from about 0.1 wt. % to about 2 wt. %, from about 0.1 wt. % to about 1 wt. %, or from about 0.3 wt. % to about 0.8 wt. %). For example, steareth-21, which is PEG-21 stearyl ether, can be present in an amount of from about 0.1 wt. % to about 2 wt. % (e.g., from about 0.1 wt. % to about 1 wt. %, from about 0.3 wt. % to about 1 wt. %, or from about 0.3 wt. % to about 0.8 wt. %).

Examples of suitable thickeners include, but are not limited to, polyether-1, PEG-150 pentaerythrityl tetrastearate, or the like, and mixtures thereof. The thickener can be present in any suitable amount. For example, the thickener can be present in an amount of from about 0.1 wt. % to about 4 wt. % (e.g., from about 0.1 wt. % to about 3 wt. %, from about 0.1 wt. % to about 2 wt. %, from about 0.5 wt. % to about 3 wt. %, from about 0.5 wt. % to about 2 wt. %, or from about 1 wt. % to about 2 wt. %).

Examples of gelling agents include, but are not limited to, disodium dimethicone copolyol sulfosuccinate, dipotassium dimethicone copolyol sulfosuccinate, or the like, and mixtures thereof. The gelling agent can be present in any suitable amount. For example, the gelling agent can be present in an amount of from about 0.1 wt. % to about 4 wt. % (e.g., from about 0.1 wt. % to about 3 wt. %, from about 0.1 wt. % to about 2 wt. %, from about 0.5 wt. % to about 3 wt. %, from about 0.5 wt. % to about 2 wt. %, or from about 1 wt. % to about 2 wt. %).

Examples of suitable emulsifiers include, but are not limited to, stearamidopropyl dimethylamine, glyceryl esters, particularly those with an HLB value of about 3 to about 4, for example, about 3.5 to about 4.0 (such as glyceryl stearate), or the like, and mixtures thereof.

The emulsifier can be present in any suitable amount. For example, the emulsifier can be present in an amount of from about 0.1 wt. % to about 5 wt. % (e.g., from about 0.1 wt. % to about 4 wt. %, from about 0.1 wt. % to about 3 wt. %, from about 0.1 wt. % to about 2 wt. %, from about 0.1 wt. % to about 1 wt. %, from about 0.1 wt. % to about 0.5 wt. %, from about 0.5 wt. % to about 3 wt. %, from about 0.5 wt. % to about 2 wt. %, or from about 1 wt. % to about 2 wt. %).

Examples of suitable preservatives include, but are not limited to, DMDM hydantoin, disodium EDTA, tetrasodium EDTA, methylparaben, imidazolidinyl urea, diazolidinyl urea, Katon CG (marketed by Rohm and Haas), Dowicil 200 (marketed by Dow Chemical), or the like, and mixtures thereof.

In addition, the hair conditioning composition of the invention can optionally include ingredients such as pH modifiers or buffers (e.g., citric acid). The hair conditioning composition can have any suitable pH. For example, the pH of the composition can be from about 3 to about 5 (e.g., from about 3.5 to about 4.5). The hair conditioning composition of the invention can also have any suitable viscosity. For example, the viscosity of the composition of the invention, which is measured at 10 rpm for 60 seconds at 25° C., can be from about 5,000 cps to about 30,000 cps (e.g., from about 6,000 cps to about 25,000 cps, from about 7,000 cps to about 25,000 cps, from about 7,000 cps to about 20,000 cps, or from about 7,000 cps to about 10,000 cps).

The quick dispersing hair conditioning composition can be prepared by any suitable method. For example, the composition can be prepared by adding the dimethicone to a solution of water and the one or more fatty alcohols, fatty amine and fatty quats added at a temperature of at least 50° C. (e.g., at least 60° C., at least 70° C., or at least 80° C.). The mixture can then be cooled to about 50° C. (e.g., about 40° C., about 45° C., about 55° C., or about 60° C.) and mixed at a suitable speed to obtain an homogeneous product. Then the isostearamidopropyl ethyldimethylammonium salt, the dicocodimethylammonium salt, or a mixture thereof can be added and mixed to obtain the composition.

The dispersion (i.e., the dispersion profile) of the composition of the invention can be determined by any suitable method. Preferably, the dispersion profile is determined by measuring the light (visible, 420 nm) transmittance of a warm water solution as a hair conditioner is dispersing at regular time intervals. For example, a beaker with a magnetic stirrer can be filled with 400 mL of warm tap water (i.e., from about 35° C. to about 40° C., e.g., 39° C.) and placed on a stirring plate with the stirrer setting at 1. Using a syringe, 1.5 mL of hair conditioning composition can be added to the water and a timer started. Every 20 seconds, a 1.5 mL aliquot can be taken from the middle of the solution and placed in cuvettes used for UV/visible transmittance. Samples can be collected every 20 seconds from 0 to 120 seconds. The samples can be evaluated for percent transmittance of light having a wavelength of 420 nm using a UV/Visible spectrophotometer.

The following examples further illustrate the invention but, of course, should not be construed as in any way limiting its scope.

Example 1

This example demonstrates hair conditioning compositions in accordance with an embodiment of the invention.

TABLE 1

| Ingredients | A wt. % | B wt. % | C wt. % | D wt. % |
|---|---|---|---|---|
| Water DI | 87.75 | 87.40 | 87.50 | 87.20 |
| Disodium EDTA | 0.02 | 0.02 | 0.02 | 0.02 |
| Citric acid USP | 0.23 | 0.23 | 0.23 | 0.23 |
| Cetyl alcohol | 2.00 | 3.00 | 3.00 | 3.00 |
| Stearyl alcohol NF | 2.00 | 1.00 | 1.00 | 1.00 |
| Steareth-21 | 0.50 | 0.50 | 0.50 | 0.50 |
| PEG-150 Pentaerythrityl-tetrastearate | 2.00 | 2.00 | 1.00 | 2.00 |
| Polyether-1 | — | — | 0.50 | — |
| Glyceryl stearate | 0.30 | 0.30 | 0.30 | 0.30 |
| Stearamidopropyl | 1.00 | 1.00 | 1.00 | 1.00 |

TABLE 1-continued

| Ingredients | A wt. % | B wt. % | C wt. % | D wt. % |
|---|---|---|---|---|
| dimethylamine | | | | |
| Quaternium-18 | 1.50 | 1.50 | 1.50 | 1.50 |
| Dimethicone | 0.60 | 0.60 | 1.00 | 0.60 |
| Quaternium-80 | 0.40 | — | — | 0.20 |
| Disodium dimethicone copolyol sulfosuccinate | 0.25 | — | — | — |
| Mackernium CC-112P9 or Arquad 2C-70 | 1.00 | 2.00 | 2.00 | 2.00 |
| Fragrance | 0.25 | 0.25 | 0.25 | 0.25 |
| DMDM hydantoin | 0.20 | 0.20 | 0.20 | 0.20 |
| | 100.00 | 100.00 | 100.00 | 100.00 |
| pH | 4.13 | 3.9 | 4.28 | 4.48 |

The compositions are prepared by heating water to 80° C. and then adding disodium EDTA. Once the disodium EDTA is dissolved, the solution is maintained at 60° C. or above and cetyl alcohol, stearyl alcohol, and steareth-21 are added and mixed. The resulting mixture is maintained at 80° C., and PEG-150 pentaerythrityl tetrastearate, polyether-1, glyceryl stearate, stearamidopropyl dimethylamine, and quaternium-18 are added. After mixing until the preparation is homogenous, dimethicone and quaternium-80 are added as indicated in the table above. The resulting mixture is then mixed at suitable speed to obtain an homogeneous composition) for 30 minutes at 85° C. and force cooled to 50° C. At 55° C., disodium dimethicone copolyol sulfosuccinate is added. At 50° C., Mackernium CC-112P9 or Arquad 2C-70 is added, and at 42° C., fragrance and DMDM hydantoin are added. The pH is adjusted to about 3.5 to about 4.5.

Example 2

This example demonstrates the dispersion profiles of the compositions labeled A, B, C, and D from Example 1. The dispersion profiles were determined by filling a 1000 mL beaker having a magnetic stirrer with 400 mL of warm tap water (i.e., from about 35° C. to about 40° C.) and placing it on a stirring plate with the stirrer setting at 1. Using a syringe, 1.5 mL of the hair conditioning composition is added to the water, and a timer is started. Every 20 seconds, a 1.5 mL aliquot is taken from the middle of the solution and placed in cuvettes used for UV/visible transmittance. Samples are collected every 20 seconds from 0 to 120 seconds. The samples are then evaluated for percent transmittance of light having a wavelength of 420 nm using a UV/Visible spectrophotometer. As shown in the FIGURE, the embodiments of the invention have high rates of dispersion in water as shown by the high rate of decrease of transmittance.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A quick dispersing hair conditioning composition comprising:
   (a) from about 1 wt. % to about 2 wt. % cationic surfactant, which is isostearamidopropyl ethyldimethylammonium ethosulfate or dicocodimethylammonium chloride;
   (b) from about 1 wt. % to about 2 wt. % additional cationic surfactant, which is monomeric, dimeric or polymeric;
   (c) from about 2 wt. % to about 3 wt. % cetyl alcohol;
   (d) from about 1 wt. % to about 2 wt. % stearyl alcohol;
   (e) from about 0.5 wt. % to about 1 wt. % dimethicone; and
   (f) from about 85 wt. % to about 90 wt. % water,
   wherein the hair conditioning composition is non-transparent and has a dispersion rate such that when 1.5 mL of the composition is dispersed into 400 mL of water at about 35° C. to about 40° C., the dispersion has a transmittance at 420 nm that is less than 70% of the water at the same temperature in less than 120 seconds.

2. The composition of claim 1, wherein the cationic surfactant is isostearamidopropyl ethyldimethylammonium ethosulfate.

3. The composition of claim 1, further comprising one or more additional ingredients, other than isostearamidopropyl ethyldimethylammonium ethosulfate and dicocodimethylammonium chloride, selected from thickeners, preservatives, gelling agents, emulsifiers, fragrances, and mixtures thereof.

4. The composition of claim 1, wherein the composition has less than 60% transmittance of the water in less than 120 seconds.

5. The composition of claim 1, wherein the composition has less than 50% transmittance of the water in less than 120 seconds.

6. The composition of claim 1, wherein the composition has less than 70% transmittance of the water in less than 100 seconds.

7. The composition of claim 1, wherein the composition has less than 70% transmittance of the water in less than 80 seconds.

8. The composition of claim 1, wherein the composition has less than 70% transmittance of the water in less than 60 seconds.

9. The composition of claim 1, wherein the hair conditioning composition has a dispersion rate such that when 1.5 mL of the composition is dispersed into 400 mL of water at 39° C., the dispersion has a transmittance at 420 nm that is less than 70% of the water at the same temperature in less than 120 seconds.

10. The composition of claim 1, wherein the composition has a pH of from about 3.5 to about 4.5.

11. The quick dispersing hair composition of claim 1, which is free of homopolymers of ethylene oxide or propylene oxide or copolymers of ethylene oxide and propylene oxide.

12. The composition of claim 1, wherein the cationic surfactant is dicocodimethylammonium chloride.

* * * * *